(12) United States Patent
Fujieda (10) Patent No.: US 6,361,168 B1
(45) Date of Patent: Mar. 26, 2002

(54) OPHTHALMIC APPARATUS

(75) Inventor: Masanao Fujieda, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/672,010

(22) Filed: Sep. 29, 2000

(30) Foreign Application Priority Data

Sep. 29, 1999 (JP) .......................................... 11-277167

(51) Int. Cl.[7] ................................................. A61B 3/14
(52) U.S. Cl. ..................................................... 351/208
(58) Field of Search ................................. 351/205, 208, 351/210, 211, 212, 221, 204

(56) References Cited

U.S. PATENT DOCUMENTS

| | | |
|---|---|---|
| 5,406,076 A | 4/1995 | Mimura et al. |
| 5,500,697 A | 3/1996 | Fujieda |
| 5,502,519 A | 3/1996 | Hosoi |
| 5,528,323 A | 6/1996 | Fujieda et al. |
| 5,532,769 A | 7/1996 | Miwa et al. |
| 5,557,350 A | 9/1996 | Yano |
| 5,757,461 A | 5/1998 | Kasahara et al. |
| 5,764,341 A | 6/1998 | Fujieda et al. |
| 5,841,502 A | 11/1998 | Miwa |
| 5,841,511 A | 11/1998 | D'Souza et al. |
| 5,889,576 A | 3/1999 | Fujieda |
| 5,905,562 A | 5/1999 | Isogai et al. |
| 5,907,388 A | 5/1999 | Fujieda |
| 6,033,075 A | 3/2000 | Fujieda |
| 6,053,614 A  * | 4/2000 | Kawamura et al. ......... 351/211 |

FOREIGN PATENT DOCUMENTS

| | | |
|---|---|---|
| EP | 0 811 352 A2 | 12/1997 |
| JP | 3-188826 | 8/1991 |
| JP | 8-103413 | 4/1996 |
| JP | 9-224911 | 9/1997 |

* cited by examiner

*Primary Examiner*—George Manuel
(74) *Attorney, Agent, or Firm*—Finnegan, Henderson, Farabow, Garrett & Dunner, L.L.P.

(57) ABSTRACT

An ophthalmic apparatus for measuring a characteristic of an eye to be examined, the apparatus comprising a moving device for relatively moving a measurement unit with respect to the eye, wherein the measurement unit includes a measurement system for measuring the characteristic of the eye, a position detecting device for detecting a relative position of the measurement unit with respect to the eye at the time of measurement, a storing device for storing detected position data, and a processing device for performing a predetermined processing based on a plurality of position data stored in each measurement.

11 Claims, 7 Drawing Sheets

OPHTHALMIC APPARATUS

BACKGROUND OF THE INVENTION

1. Field of the Invention

The present invention relates to an ophthalmic apparatus for examining or measuring an eye to be examined.

2. Description of Related Art

With an ophthalmic apparatus for obtaining data about characteristics of an eye to be examined, such as eye refractive power or corneal shape, an examinee's head is stably fixed on a head rest or the like. Thereafter, a measurement part (a measurement optical system) is aligned with the eye and then measurement is performed.

Recently, in order to save trouble of an examiner to make fine alignment, there has been suggested an apparatus having an auto-alignment mechanism which detects an alignment condition of the measurement part with respect to the eye and automatically moves the measurement part based on the thus detected result.

With this kind of apparatus, however, it is often the case where an examinee's head is inclined with respect to a horizontal reference although the examinee's head is fixed by using a head rest or the like. There is also possibility that the examinee's head may move at the time of shifting the measurement part from one eye to the other after completion of measurement on the first eye. Measurement performed under such a condition is likely to end up in inaccurate measurement results, namely astigmatic axial (cylindrical axial) angles, refractive power in the principal meridian direction, or the like. Especially in the case where refractive power data or corneal shape data is used in keratorefractive surgery for correcting refractive error by ablating the cornea using an excimer laser beam, the astigmatic axial angle data is desired to be highly accurate.

Further, with this kind of apparatus having an auto-alignment mechanism, the measurement part automatically tracks movement of the eye and the measurement is performed automatically upon completion of the alignment. Therefore, it is difficult to grasp the movement of the eye. If the eye is not stably fixed, measurement results obtained thereby will be of poor reliability.

SUMMARY OF THE INVENTION

The present invention has been made in view of the above circumstances and has an object to overcome the above problems and to provide an ophthalmic apparatus with which highly reliable measurement results are obtained.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus for measuring a characteristic of an eye to be examined, the apparatus comprises moving means for relatively moving a measurement unit with respect to the eye, wherein the measurement unit includes a measurement system for measuring the characteristic of the eye, position detecting means for detecting a relative position of the measurement unit with respect to the eye at the time of measurement, storing means for storing detected position data, and processing means for performing a predetermined processing based on a plurality of position data stored in each measurement.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1A:
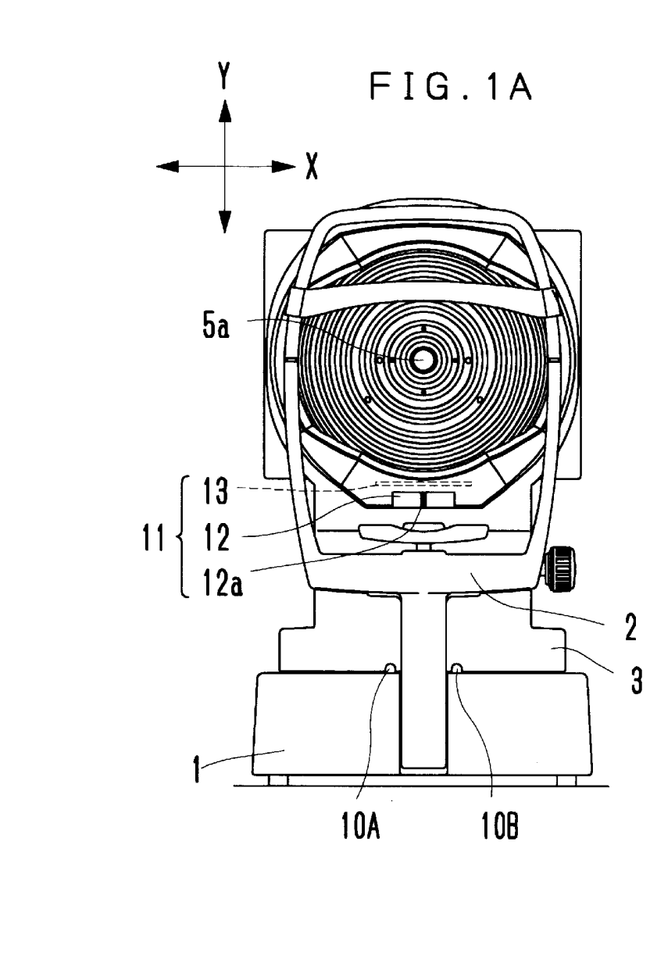
FIGS. 1A and 1B are external views showing construction of an apparatus in accordance with one preferred embodiment of the present invention.
Figure 1B:
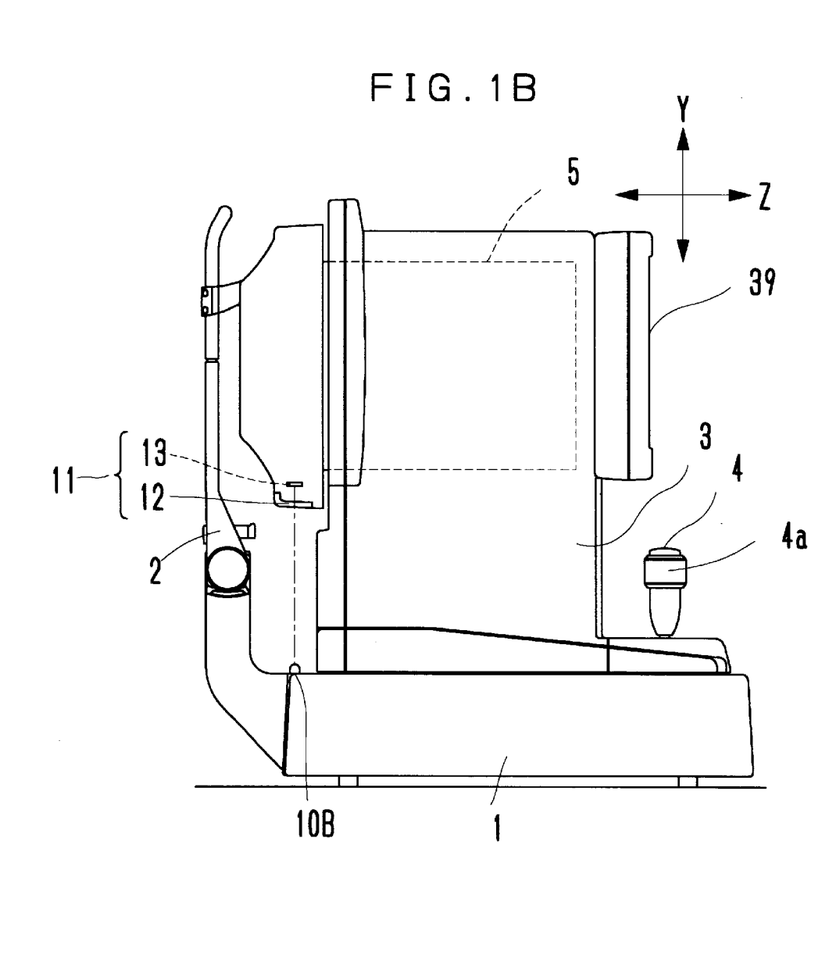
Figure 2:
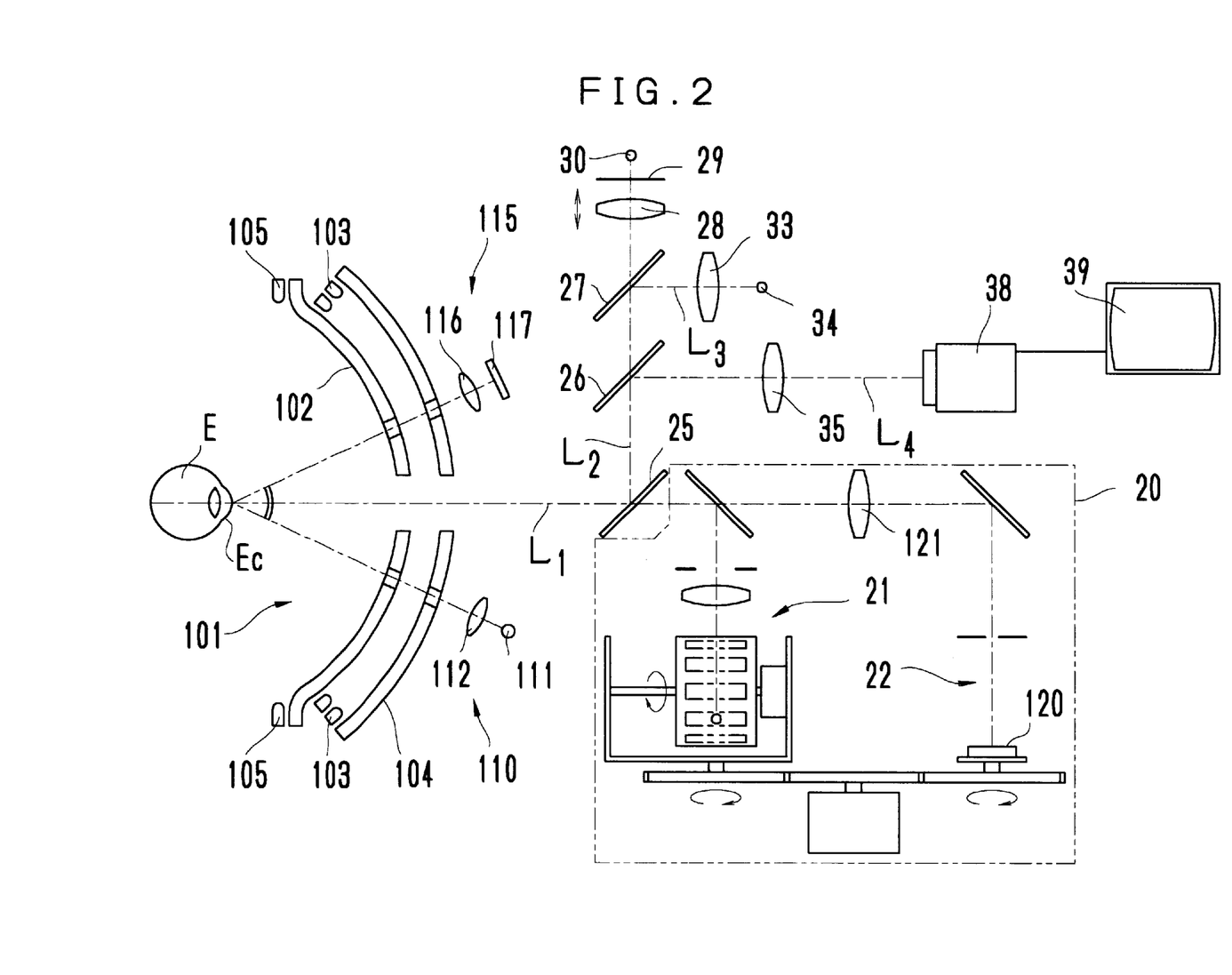
FIG. 2 is a schematic view showing construction of optical systems arranged inside a measurement part of the apparatus.
Figure 3:
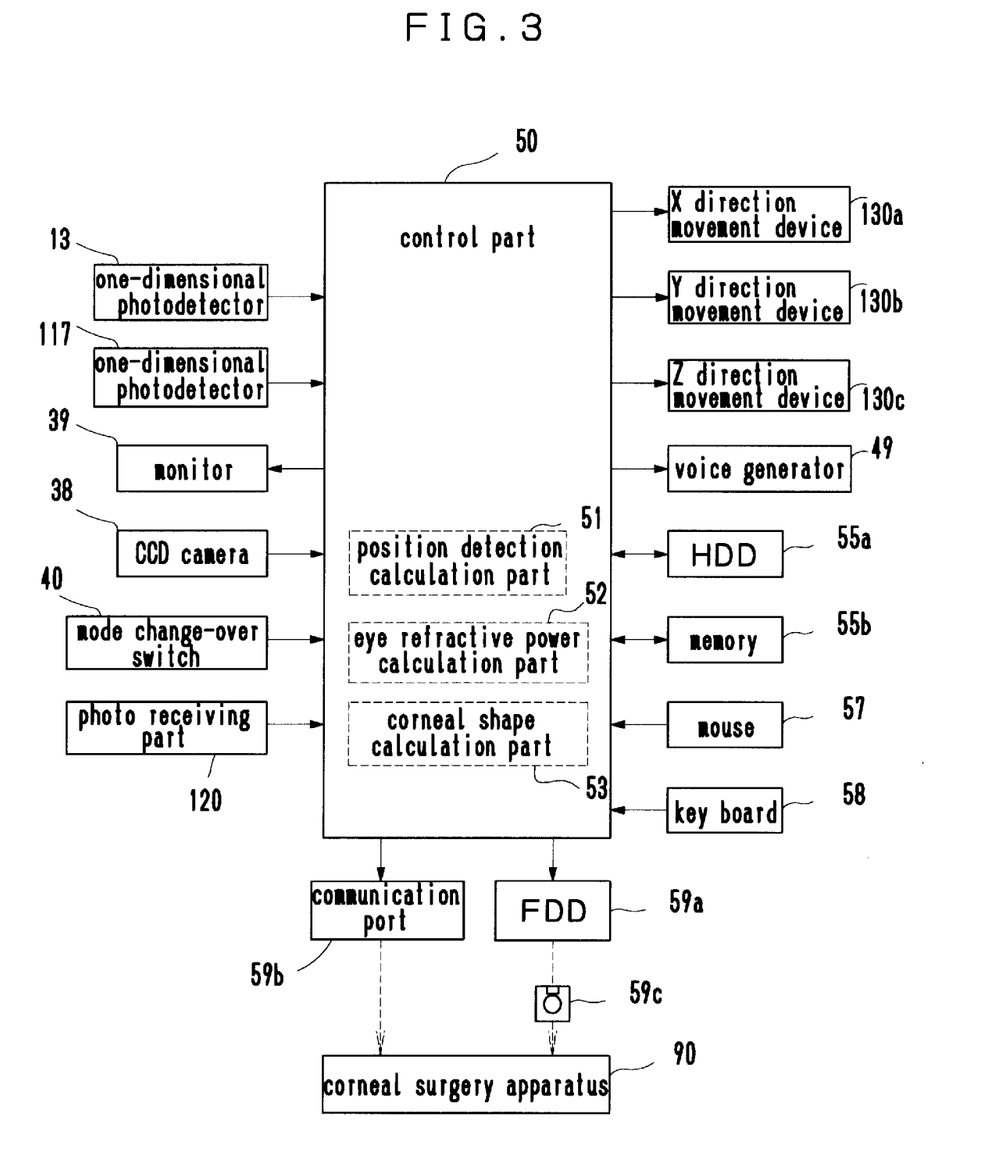
FIG. 3 is a schematic block diagram showing a control system of the apparatus.

A detailed description of one preferred embodiment of an ophthalmic apparatus embodying the present invention will now be given referring to the accompanying drawings. FIGS. 1A and 1B are external views showing construction of the apparatus in accordance with the preferred embodiment of the present invention: FIG. 1A is a front view, looking from an examinee's side and FIG. 1B is a side view. FIG. 2 is a schematic view showing construction of optical systems arranged inside a measurement part 5. FIG. 3 is a schematic block diagram showing a control system of the apparatus.

Reference numeral 1 denotes a fixed base. The base 1 has a head support part 2 fixedly attached thereto for fixedly supporting an examinee's head. 5 is the measurement part containing a measurement optical system, an alignment optical system and the like which will be described later. The measurement part 5 is provided with a measurement window 5a at an approximate center thereof in the right and left direction (X direction) on a side facing to the examinee. A main body 3 to which the measurement part 5 is mounted slides along the base 1 in the right and left direction (X direction) and the back and forth direction (Z direction) by a known slide mechanism which works in response to operation of a joystick 4. In addition, the measurement part 5 moves in the up and down direction (Y direction) relative to the main body 3 by a Y direction movement device 130b which is driven via a control part 50 in response to rotation operation of a rotation knob 4a mounted at the joystick 4. Further, to be ready for auto-alignment, the measurement part 5 is movable in the X, Y and Z directions relative to the main body 3 by the control part 50 as well as an X direction movement device 130a, the Y direction movement device 130b and a Z direction movement device 130c.

Figure 7:
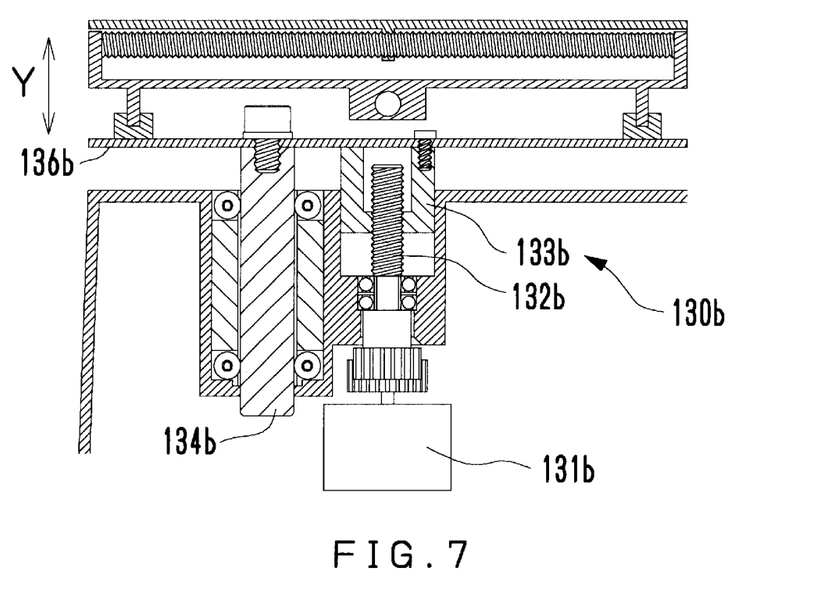
FIG. 7 is a view showing a Y direction movement device of the apparatus.
Figure 8:
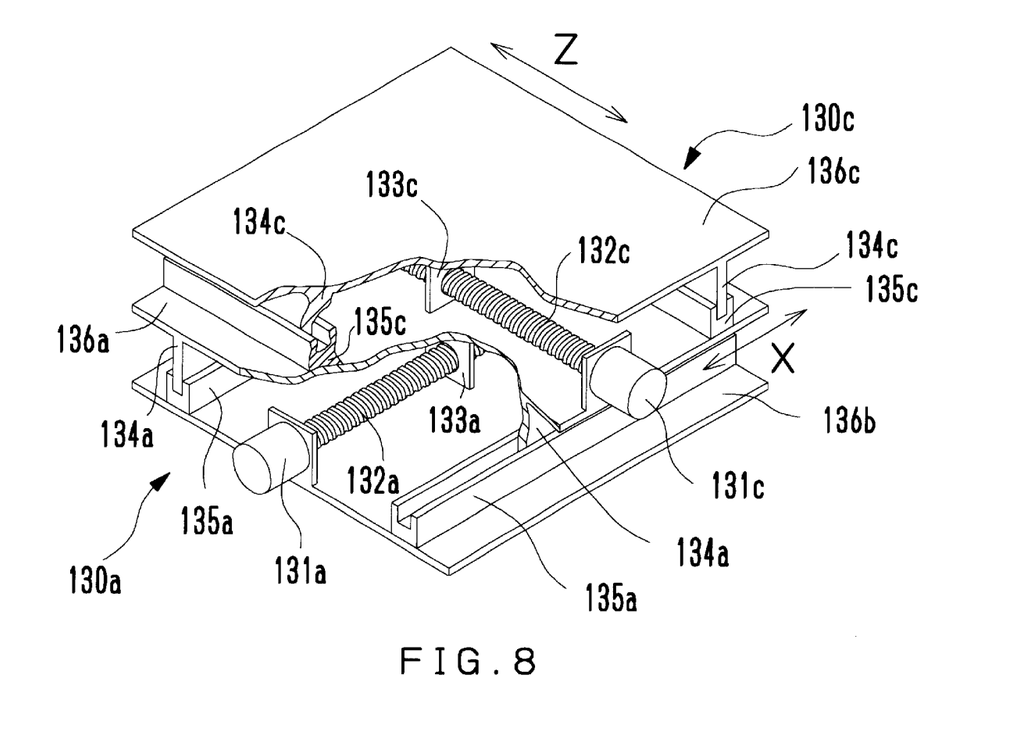
FIG. 8 is a view showing an X direction movement device and a Z direction movement device of the apparatus.

The device 130b (see FIG. 7) rotates a feed screw 132b by a pulse motor 131b fixedly provided to the main body 3, thereby causing a female screw portion 133b fixedly provided to a Y table 136b to descend and ascend. As the result, the Y table 136b moves vertically. 134b is a guide shaft fixed to the Y table 136b. The device 130a (see FIG. 8) rotates a feed screw 132a by a pulse motor 131a fixedly provided to the Y table 136b, thereby causing a female screw portion 133a fixedly provided to an X table 136a to move right and left. As the result, the X table 136a moves laterally. 135a is a guide groove fixedly provided to the Y table 136b, and 134a is a guide plate fixedly provided to the X table 136a. The device 130c (see FIG. 8) has a configuration similar to the device 130a, and through rotation of a feed screw 132c by a pulse motor 131c fixedly provided to the X table 136a, a female screw portion 133c fixedly provided to the Z table 136c is moved back and forth. As the result, the Z table 136c moves back and forth. 135c is a guide groove fixedly provided to the X table 136a, and 134c is a guide plate fixedly provided to the Z table 136c. Each of these devices 130a, 130b and 130c allows the measurement part 5 mounted on the Z table 136c to move in each of X, Y and Z directions.

Reference numeral 39 is a color monitor (display) for displaying various information to the examiner, such as an image of an eye to be examined, alignment information, measurement results and the like.

Reference numerals 10A and 10B denote light sources emitting infrared light such as LEDs or the like. The light sources 10A and 10B are arranged on the base 1 at the examinee's side with a predetermined distance therebetween and with its center at the center of the base 1 in the X direction. 11 is a photo receiving part comprised of a slit 12 and a one-dimensional photodetector (a position detector) 13. The slit 12 is arranged generally at an approximate center in the X direction and has one slit aperture 12a extending in a Z direction. The photodetector 13 has a detecting plane along the X direction.

Light emitted from each of the two light sources 10A and 10B illuminates the slit 12. Thereafter each of the light is limited by passing through the slit aperture 12a and reaches the photodetector 13. Based on incident positions of each slit light on the photodetector 13, the control part 50 detects the relative position of the measurement part 5 in the X and Y directions with respect to the base 1.

Figure 5:
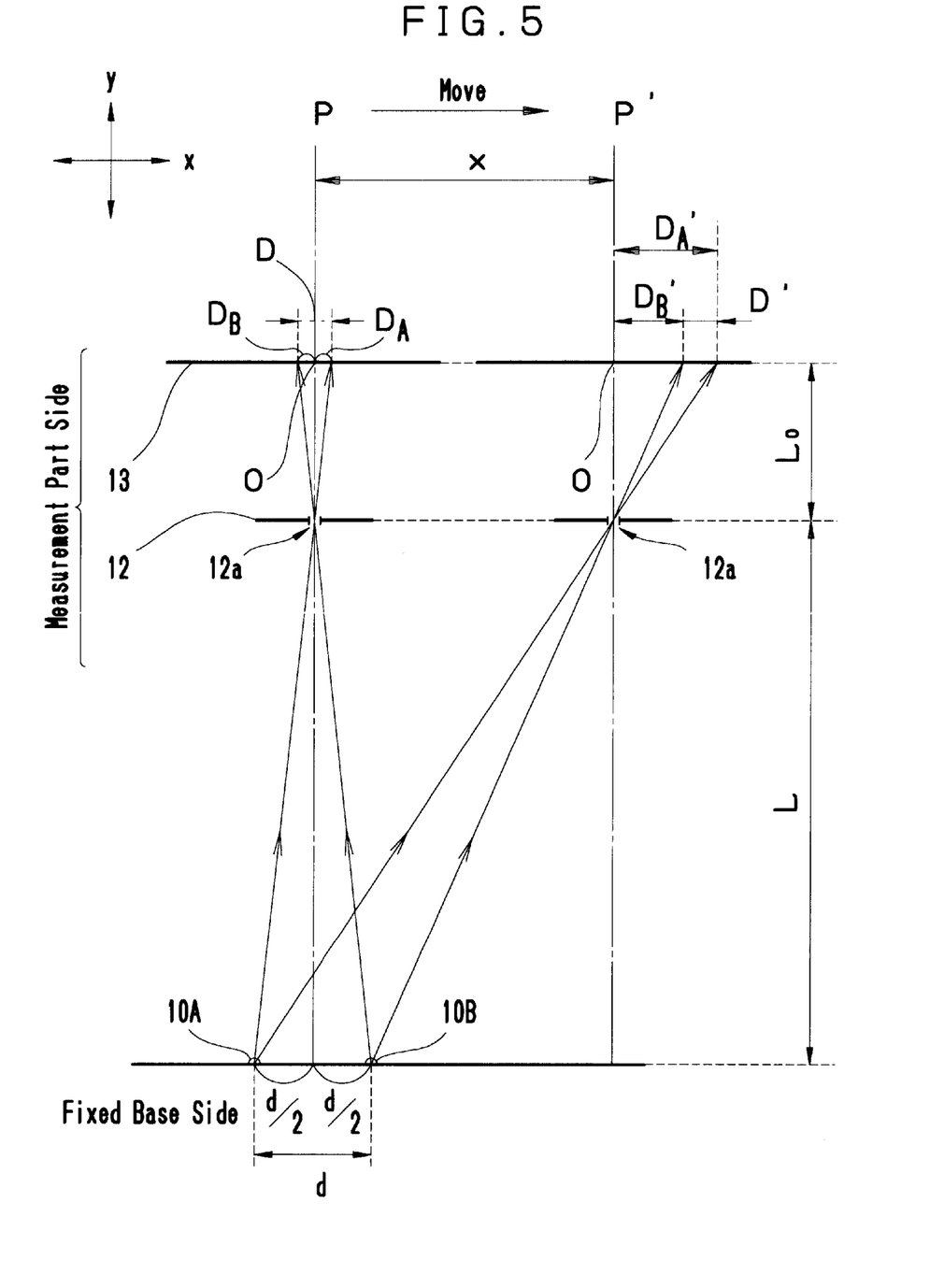
FIG. 5 is a view illustrating a way of detecting the relative position of the measurement part in up, down, right and left directions with respect to a fixed base.

Description is now given to a way of position detection of the measurement part 5 with reference to FIG. 5 (for the sake of simplicity in the description, it is supposed that the measurement part 5 is at a constant position in the Z direction and the two-dimensional position in X and Y directions needs to be detected).

First, it is supposed that a reference position P in the X direction is on a perpendicular bisector of the light sources 10A and 10B arranged to have a distance d therebetween. Then, the slit aperture 12a (i.e. the measurement part 5) moves to a position P' that is a distance x away from the position P in the X direction. In the Y direction, on the other hand, it is supposed that the slit aperture 12a (i.e. the measurement part 5) is at a position that is a distance L away from the axial line of the light sources 10A and 10B in a vertical direction, and that the distance between the slit aperture 12a and the detecting plane of the photodetector 13 is a distance Lo (predetermined distance). Here, let D' denote the distance between the incident positions of the slit light emitted from each of the light sources 10A and 10B on the photodetector 13, then the distance L is obtained by the following expression.

$$L=(d/D')\times Lo \quad \text{Expression 1}$$

Once the distance L is obtained, the travel distance x of the position P' from the reference position P is then obtained through detecting deviation of at least one of the incident positions on the photodetector 13 from a certain reference point on the photodetector 13. For example, a point O on the photodetector 13 located right above the slit aperture 12a is determined as the reference point (in the figure, the direction to the right relative to the reference point O is referred to as "+", and the direction to the left is referred to as "−"). When considering the slit light by the light source 10A is at the position P', let D'A denote the deviation amount of the incident position of the slit light to the reference point O, then judging from the figure the travel distance x is obtained by the following expression.

$$x=(L/Lo)\times D'A-(d/2)$$

By substituting the above Expression 1 into this expression, the following expression is obtained.

$$x=(D'A/D')\times d-(d/2)$$

On the other hand, when considering the slit light by the light source 10B at the position P', let D'B denote the deviation amount of the incident position of the slit light to the reference point O. Then in a like manner as the case of the light source 10A, the travel distance x is obtained by the following expression.

$$x=(D'B/D')\times d+(d/2)$$

Accordingly, through detecting and calculating the distance D' between incident positions of each slit light and the deviation amount D'A of the incident position of the slit light by the light source 10A (or alternatively the deviation amount D'B of the slit light by the light source 10B), the travel distance x of the position P' from the reference position P are obtained (preferably, an average of the deviation amounts D'A and D'B of the respective incident positions of the slit light is obtained). For the details of this position detection, see U.S. Pat. No. 5,764,341 (Japanese unexamined publication No. HEI 9 (1997)-149885).

It should be noted that in this preferred embodiment, the light sources 10A and 10B are disposed to the base 1 and the photo receiving part 11 is disposed to the measurement part 5. However, it is equally applicable to dispose the light sources 10A and 10B to the measurement part 5 and the photo receiving part 11 to the base 1. Further, it is also applicable to provide one light source and a photo receiving part having two slit apertures (See U.S. Pat. No. 5,764,341 corresponding to Japanese unexamined publication No. HEI 9 (1997)-149885).

In FIG. 2, reference numeral 101 denotes a corneal shape measurement optical system. 102 is a placido plate generally of a dome-shape having an opening at the center thereof, in which a ring pattern is formed with a number of concentric circles of light transmitting portions and light shielding portions with an optical axis L1 as the center. 103 are illumination light sources emitting light in a range between red light and infrared light such as LEDs or the like. Light emitted from the light sources 103 is reflected by a reflecting plate 104 and illuminates the placido plate 102 approximately uniformly from behind so that an image of the ring pattern (an image of the placido ring) is formed on a cornea Ec of a patient's eye E. On an outer circumference of the placido plate 102, anterior eye segment illumination lights 105 which emit near infrared light are disposed.

Disposed behind the reflecting plate 104 are a working distance target projecting optical system 110 and a working distance target detecting optical system 115: the former comprises a light source 111 emitting near infrared light such as an LED and a lens 112, and the latter comprises a lens 116 and a one-dimensional photodetector (a position detector) 117. Light emitted from the light source 111 is made generally parallel light by the lens 112 and enters into the cornea Ec obliquely through openings provided in the reflecting plate 104 and the placido plate 102, thereby forming a target image by the light source 111 on the cornea Ec. The light of the target image that has been formed on the cornea Ec passes through openings provided in the placido plate 102 and the reflecting plate 104, and enters into the photodetector 117 via the lens 116. Based on the incident position of the light of the target image on the photodetector 117, an alignment condition of the apparatus with the eye E in a working distance direction (Z direction) is detected.

Figure 4:
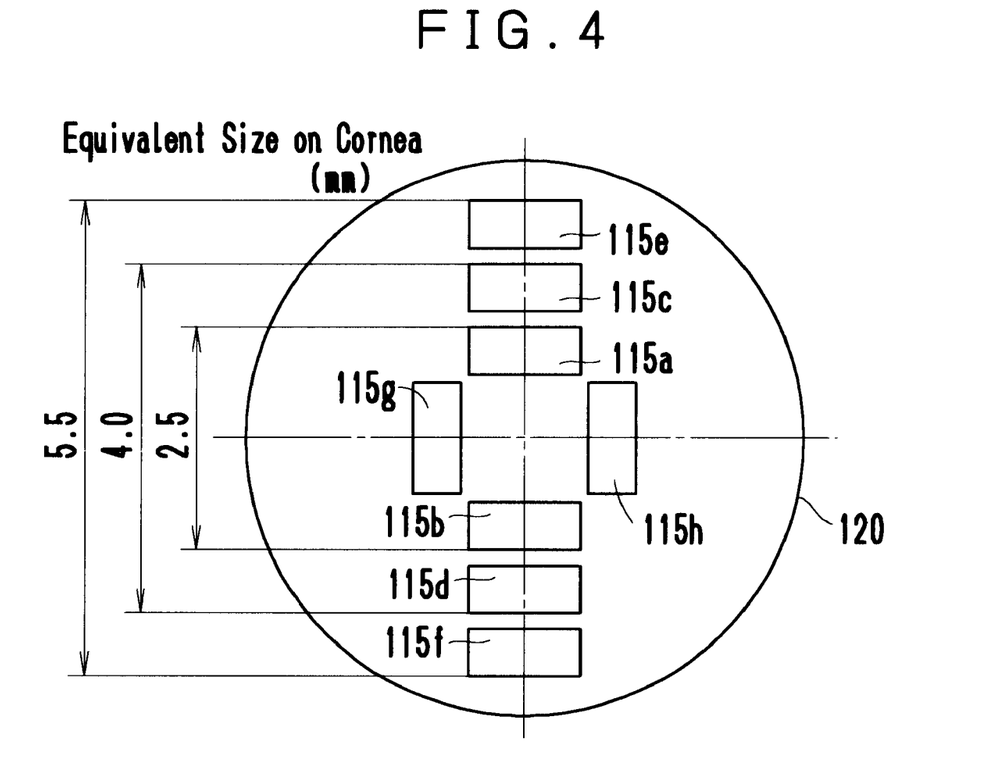
FIG. 4 is a view showing an arrangement of photodetectors included in a photo receiving part of an eye refractive power measurement optical system.

An eye refractive power measurement optical system 20 is provided in a rear direction along the optical axis L1. 120 is a photo receiving part having on its photo receiving surface eight photodetectors 115a–115h located at conjugate positions with the cornea Ec relative to a photo receiving lens 121 (see FIG. 4). Among the eight photodetectors, the photodetectors 115a–115f are located along the line passing though the center of the photo receiving surface (the optical axis L1) such that the photodetectors 115a and 115b, 115c and 115d, and 115e and 115f are symmetrical in relation to the center of the photo receiving plane. These three pairs of photodetectors are determined their configuration distances so as to be able to detect the refractive power at each corresponding position in the meridian direction on the cornea Ec (FIG. 4 is shown in the equivalent size on the cornea Ec). On the other hand, the photodetectors 115g and 115h are disposed on a line orthogonal to the photodetectors 115a–115f to be symmetrical in relation to the optical axis L1. The eye refractive power measurement optical system 20 can be of any conventional type. In this embodiment, one disclosed in U.S. Pat. No. 5,907,388 (Japanese Unexamined Patent Publication No. HEI 10 (1998)-108837) is used. Thus, based on output signals from the photodetectors 115a–115f indicating the phase difference, the refractive power, which varies along a meridian direction is obtained at a plurality of corneal portions and distribution of the eye refractive power is obtained.

In addition, a beam splitter 25 is provided on the optical axis L1. Disposed on an optical axis L2, which is made coaxial with the optical axis L1 by the beam splitter 25 are half mirrors 26 and 27, a lens 28, a fixation target plate 29 and an illumination light source 30 which emits visible light. The fixation target plate 29 has a fixation point in the middle and an area surrounding the fixation point transmits visible light. The lens 28 is movable along the optical axis L2 so as to change visibility of the fixation point on which the eye E is fixated.

Disposed on an optical axis L3, which is made coaxial with the optical axis L2 by the half mirror 27 are a lens 33, a light source 34 which emits near infrared light. Light emitted from the light source 34 is made generally parallel light by the lens 33 and enters into the cornea Ec from the front via the half mirrors 26 and 27 and the beam splitter 25, thereby forming a target image on the cornea Ec by the light source 34. The light of target image formed on the cornea Ec enters into a CCD camera 38 via the beam slitter 25, the half mirror 26 and a lens 35.

Disposed on an optical axis L4, which is made coaxial with the optical axis L2 by the half mirror 26 are the lens 35 and the CCD camera 38 serving as a photographic element. Output from the camera 38 is inputted into the monitor 39 directly or via the control part 50. An anterior eye segment of the eye E photographed by the camera 38 is displayed on the monitor 39. Also, an image of the placido ring and a target image by the light source 34 are conducted image processing by the control part 50 to obtain the corneal shape and the alignment condition in the up and down and the right and left directions (X and Y directions).

Next, description is given to operations of the apparatus. First, description is given to eye refractive power measurement. An eye refractive measurement mode is selected by using a mode change-over switch 40.

The measurement is started, for example, from the right eye. While observing an anterior eye segment of the right eye displayed on the monitor 39, the examiner operates the joystick 4 and the rotation knob 4a to slide the main body 3 in the X and Y directions and to move the measurement part 5 in the Y direction, thereby making rough alignment. Then, when the camera 38 photographs a target image formed on the cornea Ec by the light source 34, the control part 50 obtains the coordinates of the target image to detect the alignment condition in the X and Y direction. Thereafter, the control part 50 further moves the measurement part 5 relative to the eye E based on the detection result. In other words, the control part 50 drives the X direction movement device 130a and the Y direction movement device 130b to move the measurement part 5 automatically in the X and Y directions relative to the main body 3 (to perform auto-alignment). The control part 50 also detects the alignment condition in the Z direction from signals outputted from the photodetector 117, and further moves the measurement part 5 based on the detection result. In other words, the control part 50 drives the Z direction movement device 130c to move the measurement part 5 automatically in the Z direction relative to the main body 3 (to perform auto-alignment).

Once the alignment has been completed, the control part 50 stops the drive of each of the movement devices 130a, 130b and 130c and then automatically issues trigger signals to start eye refractive measurement. An eye refractive power calculation part 52 obtains the distribution of the eye refractive power from the phase difference of the output signals from each photodetector disposed in the photo receiving part 120. To meet this end, first preliminary measurement is performed as in the case of conventional phase difference method to obtain refractive power. Based on the thus obtained result, the lens 28 is moved to fog the eye E. Thereafter, based on the output signals from the photodetectors 115g and 115h that vary in response to the movement of the slit image on the photo receiving part 120, the eye refractive power calculation part 52 obtains the corneal center in the meridian direction in which the photodetectors 115a–115f are disposed. Next, based on the phase difference of the output signals from each of the photodetectors 115a–115f with respect to the thus obtained center, refractive power at a plurality of corneal portions corresponding to each photodetector is obtained. While rotating a slit light projecting optical system 21 and the photo receiving part 120 180 degrees at a predetermined angle step (1 degree) about the optical axis, the calculation to obtain refractive power is performed for each meridian at every angle step, whereby distribution of the refractive power which varies in the meridian direction is obtained (for the details, see U.S. Pat. No. 5,907,388 (Japanese unexamined publication No. HEI 10 (1998)-108837). Here, it should be noted that values of eye refractive power are obtained with the corneal vertex as the reference. The obtained data about the distribution of the eye refractive power is stored in a HDD 55a or a memory 55b.

When measurement result of the first measurement is obtained, the control part 50 again performs auto-alignment (moves the measurement part 5) based on position information of the target images obtained by the camera 38 and the photodetector 117. After completion of the auto-alignment, eye refractive measurement is performed in the same manner as the first measurement.

Eye refractive power measurement is programmed to be repeated automatically until a predetermined number (for example, five) of measurement results are obtained on one eye. When the measurement is repeated for the predetermined number of times on the right eye, the measurement is performed on the left eye for the predetermined number of times similarly to the right eye.

Every time the measurement as above is performed, a position detection calculation part 51 included in the control part 50 obtains the relative position (hereinafter referred to as a measurement point) of the measurement part 5 in the X and Y directions based on information obtained by the photodetector 13 in a manner described above. The thus obtained measurement point is stored in the memory 55b as movement history in correspondence with the order that the measurement point is obtained. When the predetermined number of measurement results on one eye or the both eyes are obtained, the movement history of the measurement points are displayed graphically on the monitor 39.

Figure 6:
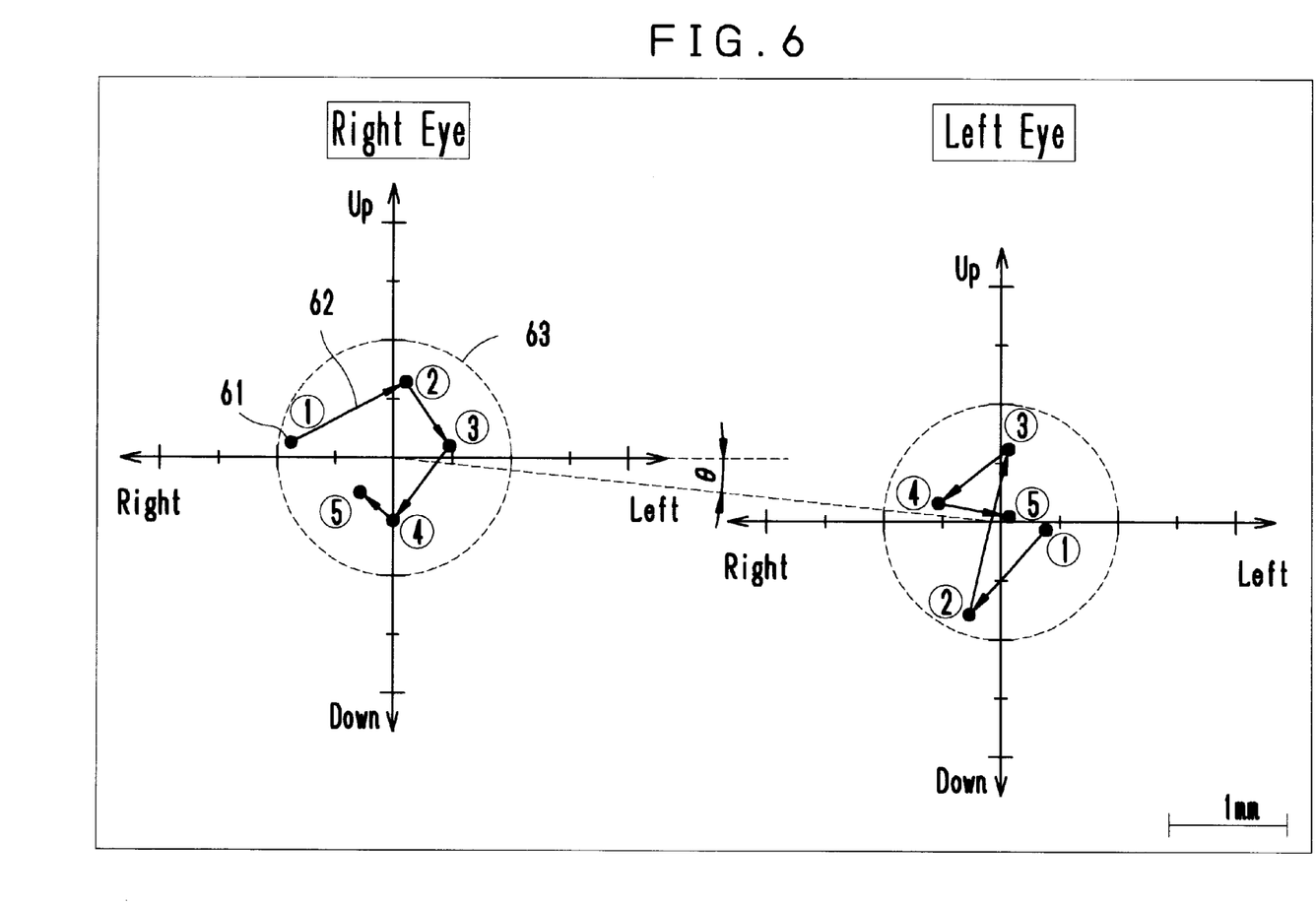
FIG. 6 is a view showing a monitor screen displaying movement history of a measurement point.

FIG. 6 shows a monitor screen displaying the movement history of the measurement points. FIG. 6 shows an example of the case where measurement is performed five times on the right eye and another five times on the left eye. The numbers indicating the order of measurement are displayed near each measurement point 61, and theses measurement points 61 are connected by arrows 62 in the order of measurement (in the figure the numbers and arrows appear as ①→②→③→④→⑤). In addition, 63 shows an allowable dispersion range of the measurement points. In the example shown in FIG. 6, the allowable dispersion range is set to have φ2 mm. Here, the allowable dispersion range 63 may be changed as the examiner intends. The allowable dispersion range 63 is set to have its center at the center of gravity of the measurement points 61. Similarly, the origin of the up and down as well as the right and left (XY coordinates) is set to be at the center of gravity of the measurement points 61. As the number of measurement points 61 increases to two points, three points and so on, the center of gravity shifts in response.

Here, when performing the measurement repeatedly for plurality of times on one eye, the control part 50 determines whether the measurement point 61 is within the allowable dispersion range 63. That is to say, the measurement point 61 is out of the allowable dispersion range 63, that situation is displayed on the monitor 39 to inform the examiner. Or the situation may be informed by means of a voice generator 49. In this way, the examiner can see if the examinee's head is not properly fixed by the head support part 2 so that the eye moves or if the eye moves so that the gaze is not stable.

When such a situation is informed, to avoid decreasing the reliability of measurement results, the examiner takes necessary steps such as instructing the examinee to firmly fix his head, and then redo the measurement. This eliminates the possibility of using measurement results that are obtained without properly fixing the eye so that accurate measurement results are obtained. Here, it is the control part 50 that determines whether or not the apparatus goes out of the allowable dispersion range. However, it is also applicable that the examiner make that determination based on the movement history of the measurement points that is graphically displayed on the monitor 39.

Here, in the case of auto-alignment, the measurement part 5 moves in response to the movement of the eye without requiring the examiner to perform fine alignment. Therefore, the examiner may not recognize the movement of the eye. Accordingly, it is desirable to display the movement history of the measurement points or to inform the determination regarding the stability of the eye fixation. It goes without saying that the similar effect is achieved also in the case of alignment performed manually.

In FIG. 6, the predetermined number of measurement points are measured within the allowable dispersion range on the right eye and the left eye respectively, a deviation angle θ from a horizontal reference line in the condition of measurement is obtained based on where the respective centers of the gravity of the measurement points 61 on right eye and left eye are located. Based on this deviation angle θ, the astigmatic axial angle as obtained in the measurement is corrected. In FIG. 6, the deviation angle θ is obtained from a distance in X and Y directions to the respective centers of the gravity of the measurement points of the right eye and the left eye. That is to say, if the examinee's head is inclined on the head support part 2, the astigmatic axial angle is based on the condition where the head is inclined. Yet, by correcting the angle with the deviation angle θ, the astigmatic axial angle will be of accurate one. In the case where the astigmatic axial angle is used in keratorefractive surgery for correcting the eye to be emmetropia, the measurement results are required to be highly accurate. Hence, the correction of the astigmatic axial angle is highly useful. In addition, it is also possible to obtain an interpupillary distance using the respective centers of gravity of the measurement points 61 on the right eye and the left eye.

When performing corneal shape measurement, a corneal shape measurement mode is selected using the switch 40. Similarly to the case of eye refractive power measurement, when alignment is completed using the auto-alignment mechanism, the light source 103 is illuminated for a predetermined period of time and an image of the ring pattern is photographed. A corneal shape calculation part 53 performs predetermined image processing on the photographed ring pattern image to detect the edge of the image. By obtaining each edge with respect to the corneal center at a predetermined angle step (1 degree), the distribution of the corneal curvature is obtained. The data about corneal curvature distribution is stored in the HDD 55a or the memory 55b.

Also in the corneal shape measurement, the predetermined number of measurement points are obtained and stored in correspondence with the order that the measurement point is measured (photographed) as movement history. The movement history is graphically displayed on the monitor 39. Further, the stability of the eye is determined. Thereafter, when measurement is completed on the both eyes, the deviation angle θ from the horizontal reference line is obtained from the center of gravity of the right eye measurement points and the center of gravity of the left eye measurement points, whereby the angle of inclination with respect to the data about distribution of the corneal curvature (the angle of inclination in meridian direction) is corrected.

Further, a continuous mode of eye refractive measurement and corneal shape measurement may be selected using the mode change-over switch 40. In this mode, the eye refractive measurement and the corneal shape measurement are continually performed on one eye. In this case too, the measurement points obtained in each measurement are stored as movement history. Based on the display of the movement history or the determination of whether the measurement point is out of the allowable dispersion range, reliability of the measurement results to be used is determined. In addition, the axial angle (the angle of inclination) of the both measurement is corrected so that even though the examinee's head is inclined, the axial data can be accurate.

By operating a mouse 57 or a key board 58, the thus obtained measurement results may be transmitted to a corneal surgery apparatus 90 via a FDD 59a (and FD 59c) and a communication port 59b. The corneal surgery apparatus 90 calculates ablation data (such as ablation amount and an ablation range) from the data transmitted thereto.

In the measurement described above, the examiner may select the measurement results based on the movement history of the measurement points obtained in respective measurement on the right eye and on the left eye. For example, the data obtained when a measurement point has relatively large deviation may be excluded. Alternatively, data obtained when the measurement points are relatively stable is designated to by used in calculation of the corrective value for the astigmatic axial angle (the inclination angle). Certainly, this exclusion and designation may be done by the control part 50.

As has been described above, according to the present invention, highly reliable measurement results are obtained.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for measuring a characteristic of an eye to be examined, the apparatus comprising:
   moving means for relatively moving a measurement unit with respect to the eye, wherein the measurement unit includes a measurement system for measuring the characteristic of the eye;
   measurement control means for sequentially performing plural measurements of the eye based on a detected result of an alignment condition between the eye and the measurement unit;
   position detecting means for detecting a displacement of the measurement unit with respect to the eye at a time of each measurement;
   storing means for storing detected displacement data for each measurement time in accordance with each measurement result; and
   processing means for processing the stored displacement data to obtain a middle value and for obtaining a degree of eye fixation during the plural measurements.

2. The ophthalmic apparatus according to claim 1 further comprising a display device, and
   wherein the processing means sets a permissible range of a variation of the displacement and causes the display device to graphically display on a screen the displacement data with respect to the set permissible range.

3. The ophthalmic apparatus according to claim 2, wherein the processing means causes the displacement data to be displayed together with an order of detection.

4. The ophthalmic apparatus according to claim 1, further comprising an informing device for informing visually or audibly, and
   wherein the processing means sets a permissible range of the variation of the displacement, judges whether the displacement data deviates from the permissible range, and controls the informing device to give a warning when a deviation is found.

5. The ophthalmic apparatus according to claim 1, wherein the processing means sets a permissible range of the variation of the displacement, judges whether the displacement data deviates from the permissible range, and selects each of the obtained measurement results when a deviation is found.

6. The ophthalmic apparatus according to claim 1, wherein the processing means corrects the obtained measurement result based on the stored displacement data.

7. The ophthalmic apparatus according to claim 1, further comprising a fixed base with a support portion fixedly attached thereto for fixedly supporting an examinee's head, and
   wherein the measurement unit is moved by the moving means with respect to the fixed base.

8. The ophthalmic apparatus according to claim 7, wherein the position detecting means comprises a slit aperture and a photodetector both arranged to the measurement unit as well as a light source arranged to the fixed base, or the position detecting means alternatively comprises a slit aperture and a photodetector both arranged to the fixed base as well as a light source arranged to the measurement unit.

9. The ophthalmic apparatus according to claim 1 further comprising:
   alignment condition detecting means for detecting alignment condition of the measurement unit with the eye; and
   movement control means for controlling the moving means based on a detection result by the alignment condition detecting means.

10. The ophthalmic apparatus for measuring a characteristic of an eye to be examined, the apparatus comprising:
    moving means for relatively moving a measurement unit with respect to the eye, wherein the measurement unit includes a measurement system for measuring the characteristic of the eye;
    position detecting means for detecting each relative position of the measurement unit with respect to each of right and left eyes at each of plural measurements of the eyes;
    storing means for storing each detected relative position with respect to the right and left eyes; and
    correcting means for correcting an astigmatic axial angle or an angle of inclination of a measurement result based on the stored relative position.

11. The ophthalmic apparatus for measuring a characteristic of an eye to be examined, the apparatus comprising:
    moving means for relatively moving a measurement unit with respect to the eye, the measurement unit having a measurement system for measuring a characteristic of the eye,
    wherein the measurement system includes at least one of an eye refractive power measurement optical system and a corneal shape measurement optical system;
    measurement control means for sequentially performing plural measurements of the eye based on a detected result of an alignment condition between the eye and the measurement unit;
    position detecting means for detecting a displacement of the measurement unit with respect to the eye at each measurement;

storing means for storing detected displacement data for each measurement in accordance with each measurement result; and processing means for processing the stored displacement data to obtain a central value and for obtaining a degree of eye fixation during the plural measurements.
  wherein the measurement system includes at least one of an eye refractive power measurement optical system and a corneal shape measurement optical system;

measurement control means for sequentially performing plural measurements of the eye based on a detected result of an alignment condition between the eye and the measurement unit;

position detecting means for detecting a displacement of the measurement unit at each measurement;

storing means for storing detected displacement data for each measurement in accordance with each measurement result; and processing means for processing the stored displacement data to obtain a central value and for obtaining a degree of eye fixation during the plural measurements.

* * * * *

UNITED STATES PATENT AND TRADEMARK OFFICE
CERTIFICATE OF CORRECTION

PATENT NO. : 6,361,168 B1
DATED : March 26, 2002
INVENTOR(S) : Masanao Fujieda

It is certified that error appears in the above-identified patent and that said Letters Patent is hereby corrected as shown below:

Column 11,
Lines 7 through 12, should be deleted in their entirety.

Column 12,
Lines 1 through 10, should be deleted in their entirety.

Signed and Sealed this

Twenty-seventh Day of August, 2002

Attest:

Attesting Officer

JAMES E. ROGAN
Director of the United States Patent and Trademark Office